United States Patent [19]

Kokubo et al.

[11] Patent Number: 4,980,287
[45] Date of Patent: Dec. 25, 1990

[54] 4H-3,1-BENZOXAZIN-4-ONE COMPOUNDS AND PHARMACEUTICAL COMPOSITIONS THEREOF FOR THE INHIBITION OF SERINE PROTEASES

[75] Inventors: Masayuki Kokubo, Hino; Katsuhiko Fujii, Hachioji; Jun-ichi Oshida, Hino; Koji Tomimori, Hachioji; Yasuhide Uejima, Hino, all of Japan

[73] Assignee: Teijin Limited, Osaka, Japan

[21] Appl. No.: 340,097

[22] PCT Filed: Jun. 9, 1988

[86] PCT No.: PCT/JP88/00556
§ 371 Date: Feb. 3, 1989
§ 102(e) Date: Feb. 3, 1989

[87] PCT Pub. No.: WO88/09790
PCT Pub. Date: Dec. 15, 1988

[30] Foreign Application Priority Data

Jun. 9, 1987 [JP] Japan ................... 62-142364
Apr. 27, 1988 [JP] Japan ................... 63-102404

[51] Int. Cl.$^5$ ............... C07D 265/10; C12N 9/99; A61H 37/00; A61H 31/535
[52] U.S. Cl. .......................... 435/184; 514/2; 514/18; 514/19; 514/230.2; 530/331; 544/92; 544/93
[58] Field of Search ............ 544/92, 93; 514/230.5, 514/2, 18, 19; 530/331; 435/184

[56] References Cited

U.S. PATENT DOCUMENTS 4,657,893 4/1987 Krantz et al. .................. 514/230.5

FOREIGN PATENT DOCUMENTS 464926 12/1968 Switzerland ................... 544/93

OTHER PUBLICATIONS

Teshima et al., Journal of Biological Chemistry, 257(9), 1982, pp. 5085-5891.
Spencer et al., Biochem. Biophys. Research Commun., 140(3), 1986, pp. 928 to 933.
Hedstrom et al., Biochemistry 23, 1984, 1753-1759.
Krantz et al., J. Mec. Chem., 1990, 33, 464-479.

Primary Examiner—Mukund J. Shah
Assistant Examiner—E. C. Ward
Attorney, Agent, or Firm—Sughrue, Mion, Zinn, Macpeak & Seas

[57] ABSTRACT

A 4H-3,1-benzoxazin-4-one compound of the formula (I):

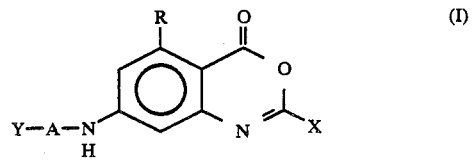

wherein R is a hydrogen atom or alkyl radical, A is an amino acid residue or a peptide having 2 to 3 amino acid residues, which amino acid residue may have a side chain thereof protected by a protective radical, X is an alkyl, fluoroalkyl, OR$^1$ or NHR$^1$ radical wherein R$^1$ is an alkyl radical, and Y is a protective radical for an amino radical, and salts thereof, exhibit an excellent inhibitory activity against serine proteases, especially against human leukocyte elastase, and thus are useful as an effective component of a medicine for inhibiting elastase.

5 Claims, No Drawings

4H-3,1-BENZOXAZIN-4-ONE COMPOUNDS AND PHARMACEUTICAL COMPOSITIONS THEREOF FOR THE INHIBITION OF SERINE PROTEASES

DESCRIPTION

1. Technical Field

The present invention relates to 4H-3,1-benzoxazin-4-one compounds and pharmaceutical compositions containing same as an effective component for inhibiting serine proteases.

More particularly, the present invention relates to 4H-3,1-benzoxazin-4-one compounds useful for blocking degeneration, destruction or inflammation of tissues caused by the action of proteases, especially, elastase, on mammalian proteins such as elastin, and pharmaceutical compositions containing same as an effective component for inhibiting serine proteases, especially elastase.

2. Background Art

Elastin is a fibrous protein which forms a principal component of elastic fibers in connective tissues and has a rubber-like elasticity, and is contained in a large amount in lungs, bronchi, and aortas.

Elastase is a group of proteases capable of hydrolyzing elastin, and is produced in pancreata and polymorphonuclear leukocytes of mammals or by certain types of microorganisms. The elastase produced in the leukocytes plays an important role in the digestion of phagocytosed bacteria, but when leaked from the cell to the outside, the elastase attacks tissue elastin and causes degeneration, destruction or inflammation of tissues.

This excessive digestion of elastin by the elastase is considered to be a cause of pulmonary emphysema, adult respiratory distress syndrome, pulmonary fibrosis, bronchitis, pneumonia, rheumatoid arthritis, arteriosclerosis, sepsis, shock, pancreatitis, nephritis, and certain dermatosis.

Accordingly, an elastase inhibitor is considered to be useful as a remedy or preventive for the abovementioned diseases.

A group of 4H-3,1-benzoxazin-4-one compounds having, as a basic structure, the chemical formula:

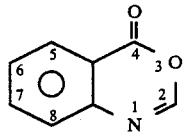

are known substances capable of inhibiting serine proteases.

For example, Teshima et al. (J. BIOL. CHEM., vol. 257, pages 5085 to 5091 (1982)) reported various types of 2-alkyl-4H-3,1-benzoxazin-4-one compounds and Hedstrom et al. (BIOCHEMISTRY, vol 23, pages 1753 to 1759 (1984)) reported 2-ethoxy-4H-3,1-benzoxazin-4-one. Also, Spenser et al. (BIOCHEM. BIOPHYS. RES. COMMUN., vol. 140, pages 923 to 933 (1986)) reported that 5-methyl substituted 2-alkyl-4H-3,1-benzoxazin-4-one exhibits a strong elastase inhibitory activity.

Furthermore, Japanese Unexamined Patent Publication (Kokai) No. 60-169467 for Syntax Inc., published on Sept. 2, 1985 discloses 2-amino derivatives of 4H-3,1-benzoxazin-4-one, and Japanese Unexamined Patent Publication No. 62-30770 for Syntex Inc., published on Feb. 9, 1987 discloses 2-oxy derivatives of 4H-3,1-benzoxazin-4-one.

It is known that most of the above-mentioned compounds exhibit a higher inhibiting activity for chymotrypsin than for elastase.

DISCLOSURE OF THE INVENTION

An object of the present invention is to provide 4H-3,1-benzoxazin-4-one compounds having a strong inhibitory activity against serine proteases and pharmaceutical compositions containing the same as an effective component for inhibiting serine proteases.

Another object of the present invention is to provide 4H-3,1-benzoxazin-4-one compounds having a high inhibitory activity selective for the elastase among serine proteases, and pharmaceutical compositions containing the same as an effective component for inhibiting the elastase.

The above-mentioned objects are attained by the compound of the present invention.

The 4H-3,1-benzoxazin-4-one compound of the present invention is of the formula (I):

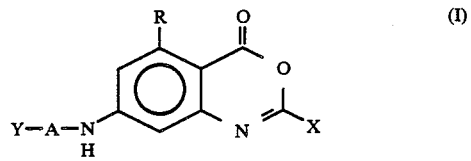

wherein R represents a member selected from hydrogen atom and alkyl radicals, A represents a member selected from amino acid residues and peptides having 2 to 3 amino acid residues, which amino acid residues may have side chains protected by protective radicals, X represents a member selected from alkyl radicals, fluoroalkyl radicals, and radicals of the formulae $OR^1$ and $NHR^1$ in which $R^1$ represents an alkyl radical, and Y represents a protective radical for an amino radical, and salts thereof.

The pharmaceutical composition of the present invention for inhibiting serine proteases comprises a mixture of a pharmaceutically effective amount of a 4H-3,1-benzoxazin-4-one compound of the above-mentioned formula (I) or a pharmaceutically acceptable non-toxic salt thereof and a pharmaceutically acceptable carrier.

BEST MODE FOR CARRYING OUT THE INVENTION

In the formula (I), the alkyl radicals represented by R preferably have 1 to 6 carbon atoms. The alkyl radicals are preferably selected from methyl, ethyl, propyl, butyl, pentyl, and hexyl radicals and isomeric radicals of the above-mentioned radicals.

Generally, more preferably the alkyl radical represented by R in the formula (I) is methyl or ethyl radical.

In the formula (I), the amino acid residues or amino acid residues contained in the peptide represented by A include residues of D- and L-optical isomers and racemic mixtures of α-, β- and γ-aminocarboxylic acids. For example, the amino acid is preferably selected from D- and L-optical isomers and racemic mixtures of alanine, asparagine, aspartic acid, cysteine, cystine, glutamic acid, glutamine, glycine, histidine, isoleucine, leucine, lysine, methionine, phenylalanine, proline, serine, threonine, tryptophan, tyrosine, valine, homoserine, homocysteine, hydroxyproline, ornithine, thyroxine, norvaline, norleucine, phenylglycine, β-alanine, and γ-aminobutyric acid.

More preferably, the amino acid is selected from L-alanine, glycine, L-isoleucine, L-leucine, L-phenylalanine, L-proline, L-valine, L-norvaline, L-norleucine, L-phenylglycine, L-lysine having an ε-amino radical protected by a carbobenzoxy radical, L-aspartic acid having a β-carboxyl radical protected in the form of a benzylester, and L-glutamic acid having a γ-carboxyl radical protected in the form of a benzylester.

In the formula (I), the side chains of amino acid residues represented by A may be protected by protective radicals. The various protective radicals for the side chains (amino, carboxyl, guanidino, imidazolyl, mercapto or hydroxyl radical) of the amino acid residues represented by (A), and the various protective radicals of amino radical represented by Y in the formula (I), are known in the art. For example, as the protective radicals for the amino radical, carbobenzoxy, succinyl, methoxysuccinyl, acetyl, trifluoroacetyl, tert-butoxycarbonyl, isonicotinylhydroxycarbonyl, and tosyl radicals are known.

Also, as the protective radicals for the carboxyl radical, for example, benzyl ester and 4-picolylester radicals are known.

Further, as the protective radicals for the guanidino and imidazolyl radicals, carbobenzoxy and tosyl radicals are known.

Still further, as the protective radical for the mercapto radical, S-benzyl radical is known, and as the protective radical for the hydroxyl radical, O-benzyl radical is known.

The protective radicals usable for the present invention are not limited to the above-mentioned radicals.

In the formula (I), the protective radicals for the amino radical represented by Y are preferably selected from carbobenzoxy, tert-butoxycarbonyl and acetyl radicals.

In the formula (I), the alkyl radical represented by X preferably has 1 to 8 carbon atoms and is selected from methyl, ethyl, propyl, butyl, isobutyl, pentyl, hexyl, heptyl and octyl radicals, and isomeric radicals of the above-mentioned alkyl radicals.

In the formula (I), the fluoroalkyl radical represented by X preferably has 1 to 4 carbon atoms, and is, for example, trifluoromethyl radical.

In the $OR^1$ radical represented by X in the formula (I), the $R^1$ radical preferably has 1 to 8 carbon atoms. The $OR^1$ radical is preferably selected from methoxy, ethoxy, propoxy, butoxy, pentoxy, hexaoxy, heptoxy and octoxy radicals, and isomeric radicals of the above-mentioned radicals.

In the $NHR^1$ radical represented by X in the formula (I), the $R^1$ radical is the same as mentioned above. The NHR radical is preferably selected from monomethylamino, monoethylamino, monopropylamino, monoisopropylamino, monobutylamino, monopentylamino, monohexylamino, monoheptylamino and monoctylamino radicals, and isomeric radicals of the above-mentioned radicals.

The salts, especially pharmaceutically acceptable salts, of the compounds of the formula (I) include salts of organic and inorganic bases attached to carboxyl radicals contained in side chains of amino acid residue or amino acid residues in peptides, of the compound of the formula (I), and salts of organic and inorganic acids attached to amino, guanidino, or imidazolyl radicals contained in the above-mentioned side chains.

The salts derived from the inorganic bases include ammonium, potassium, sodium, calcium and magnesium salts. The salts derived from the organic bases include diethylamine, isopropylamine, ethanolamine and piperidine salts. The acid-addition salts include salts derived from inorganic acids, for example, hydrochloric acid, hydrobromic acid, sulfuric acid, nitric acid and phosphoric acid and salts derived from organic acids, for example, acetic acid, propionic acid, glycollic acid, pyruvic acid, oxalic acid, malic acid, malonic acid, succinic acid, maleic acid, fumaric acid, tarturic acid, citric acid, benzoic acid, cinnamic acid, methanesulfonic acid, ethanesulfonic acid, p-toluenesulfonic acid and salicylic acid.

The 4H-3,1-benzoxazin-4-one compounds of the formula (I) of the present invention can be synthesized via the following synthetic path.

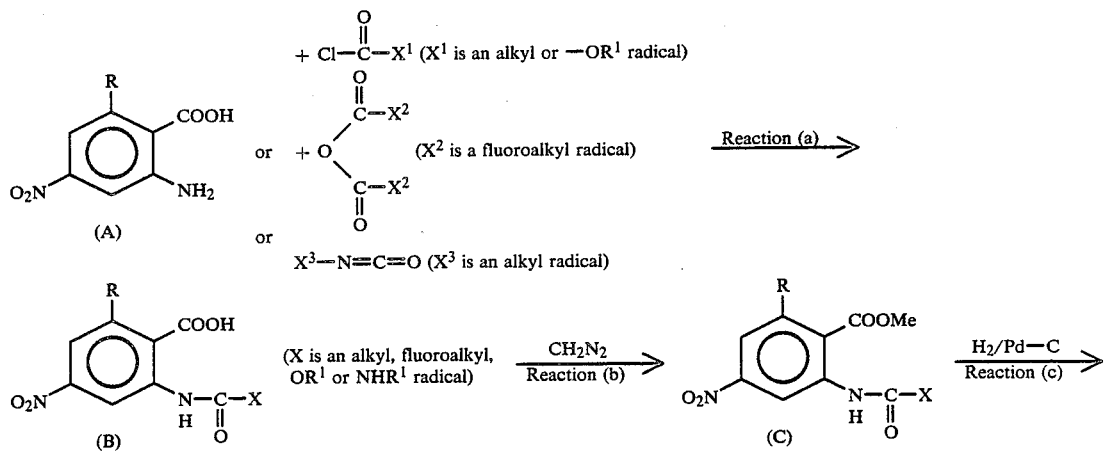

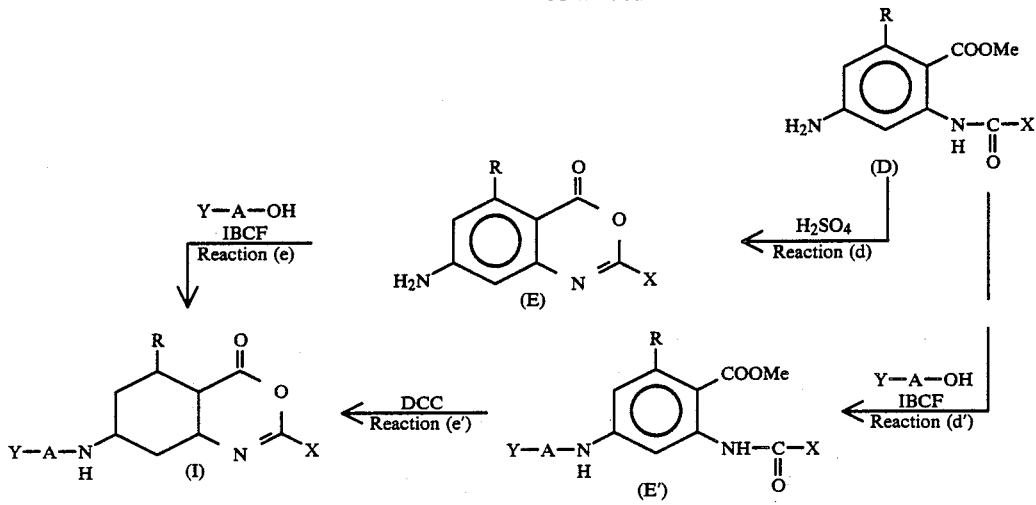

Where a compound of the formula (I) in which X represents an alkyl radical is produced, in the reaction (a), a substituted or unsubstituted 4-nitro-anthranilic acid of the formula (A) reacts with a certain aliphatic carboxylic acid chloride (ClCOX$^1$) to produce an N-acyl-4-nitroanthranilic acid of the formula (B).

Where a compound of the formula (I), in which X represents a fluoroalkyl radical is produced, in the reaction (a), a substituted or unsubstituted 4-nitroanthranilic acid of the formula (A) reacts with an aliphatic fluorohydrocarbon acid anhydride of the formula:

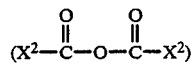

to provide a compound of the formula (B).

The above-mentioned reaction procedures are disclosed by Teshima et al. (J. BIOL. CHEM., vol. 257, pages 5085 to 5090 (1982)).

When a compound of the formula (I) wherein X represents an OR$^1$ radical, R$^1$ representing an alkyl radical, is produced, in the reaction (a), a substituted or unsubstituted 4-nitroanthranilic acid of the formula (A) reacts with a chlorocarbonate (Cl-CO-OR$^1$) to provide a carbamate compound of the formula (B). This reaction procedure is disclosed by Hedstrom et al. BIOCHEMISTRY, vol 23, pages 1753 to 1759 (1984) or by Blank et al. (J. CHEM. ENG. DAT., vol 13, pages 577 to 579 (1968)).

When a compound of the formula (I) in which X represents a NHR$^1$ radical is produced, in reaction (a), a substituted or unsubstituted 4-nitroanthranilic acid of the formula (A) reacts with a certain alkyl isocyanate (X$^3$—N=C=O) to provide a 2-(3-alkylureido)-4-nitroanthranilic acid of the formula (B). This reaction procedure is disclosed by Papadopoulos et al. (J. HETEROCYCLIC CHEM., vol. 19, pages 269 to 272 (1982)).

If necessary, in the reaction (b), the substituted or unsubstituted 4-nitroanthranilic acid derivatives of the formula (B) are converted to a methyl ester of 4-nitroanthranilic acid derivative of the formula (C) by a known method. The reaction (b) can be carried out by treating the compound of the formula (B) with diazomethane in an inert organic solvent at a temperature of about 0° C.

In the reaction (c), the substituted or unsubstituted 4-nitroanthranilic acid derivative of the formula (C) is converted to a substituted or unsubstituted 4-aminoanthranilic acid derivative of the formula (D) by a conventional method. Preferably, the reaction (c) is carried out by a catalytic hydrogenation (catalytic reduction with hydrogen gas) in the presence of a palladium-carbon catalyst.

The compound of the formula (D) can be converted to a 4H-3,1-benzoxazin-4-one compound of the formula (I) by the reactions (d) and (e) or by the reactions (d') and (e').

Where X in the formula (D) represents an NHR$^1$ radical, in the reaction (d), the anthranilic acid derivative of the formula (D) is cyclized with a dehydration-condensation agent, for example, H$_2$SO$_4$, to provide a substituted or unsubstituted 7-amino-4H-3,1-benzoxazin-4-one compound of the formula (E). Preferably, in the reaction (d), the compound of the formula (D) is treated in a concentrated sulfuric acid at room temperature to produce the compound of formula (E).

Next, in the reaction (e) the amino radical of the compound of the formula (E) is condensed with a carboxyl radical of a reactant (Y—A—OH) consisting of amino acid or peptide having protected amino radical(s), to provide a 7-(N—A—Y)amino-4H-3,1-benzoxazin-4-one compound of the formula (I).

The above-mentioned condensation reaction (e) can be carried out by various methods known for the formation of peptide bonds in a peptide synthesis (Nobuo Izumiya et al., BASIS AND EXPERIMENT OF PEPTIDE SYNTHESIS", published in 1985 by Maruzen).

In this condensation reaction (e), preferably the carboxyl radical of the amino acid or peptide having protected amino radical(s) is activated and then is condensed with the substituted or unsubstituted 4H-3,1-benzoxazin-4-one compound of the formula (E) produced by the reaction (d). In a more preferable condensation reaction method, a mixed acid anhydride is prepared by reacting an amino acid or peptide having protected amino radical(s) with a monoalkyl chlorocarbonate, and then the mixed acid anhydride is reacted with the compound of the formula (E). A preferable monoalkyl chlorocarbonate usable for the above-mentioned method is isobutyl chloroformate (IBCF).

When the A in the formula (I) represents a peptide having 2 or 3 amino acid residues, it is possible that, after the amino acid residue of the reactant Y—A—OH having protected amino radicals is condensed with the compound of the formula (E) by the reaction (e), at least one protective radical is selectively removed from the protected amino radicals by a conventional method, and the liberated free amino radical of the resultant compound is condensed again with a carboxyl radical of an amino acid having protected amino radical(s). By repeating the above-mentioned procedures, the peptide chain can be extended.

A preferable protective radical for the amino radical is a carbobenzoxy radical. The removal of the carbobenzoxy radical can be effected by a catalytic reduction with hydrogen gas in the presence of a palladium-carbon catalyst. But if this catalytic hydrogenation method is applied to lysine having an ε-amino radical protected by a carbobenzoxy radical, aspartic acid having a β-carboxyl radical protected in the form of a benzylester thereof or glutamic acid having a γ-carboxyl radical protected in the form of a benzylester thereof, the side chain-protecting radical is undesirably removed. Thus the catalytic hydrogenating method is not adequate for the above-mentioned amino acids.

Another preferable protective radical for the amino radical is a tert-butoxycarbonyl radical. This protective radical can be selectively removed by treating with trifluoroacetic acid.

Where in the formula (D), X represents an alkyl radical, fluoroalkyl radical or —OR$^1$ radical, in the reaction (d') the substituted or unsubstituted 4-aminoanthranilic acid compound of the formula (D) is converted to a compound of the formula (E') by condensing a carboxyl radical of an amino acid or peptide (Y—A—OH) having protected amino radical(s) with an amino radical of the compound of the formula (D). This condensation reaction (d') can be effected in the same manner as in the reaction (e).

Next, in the reaction (e'), the antranilic acid compound of the formula (E') is cyclized with a dehydration-condensation agent to provide a final compound of the formula (I). In the reaction (e'), the dehydration-condensation agent preferably consists of N,N'-dicyclohexylcarbodiimide (DCC).

A starting compound of the formula (A) in which R represent hydrogen atom can be easily obtained commercially. Also, amino acids having an amino radical protected by carbobenzoxy radical or tert-butoxycarbonyl radical or another amino acids having protected side chains can be easily obtained commercially.

Further, an amino acid having an amino radical protected by a methoxysuccinyl radical can be produced from a monomethyl succinate ester which can be easily obtained commercially, and a corresponding amino acid by a conventional peptide bond-forming reaction.

A starting compound of the formula (A) in which R represents an alkyl radical, that is, 4-nitro-6-alkyl anthranilic acid, can be produced by the following reactions.

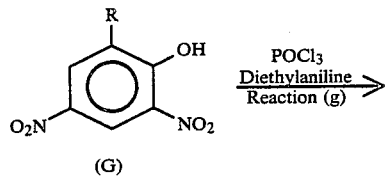

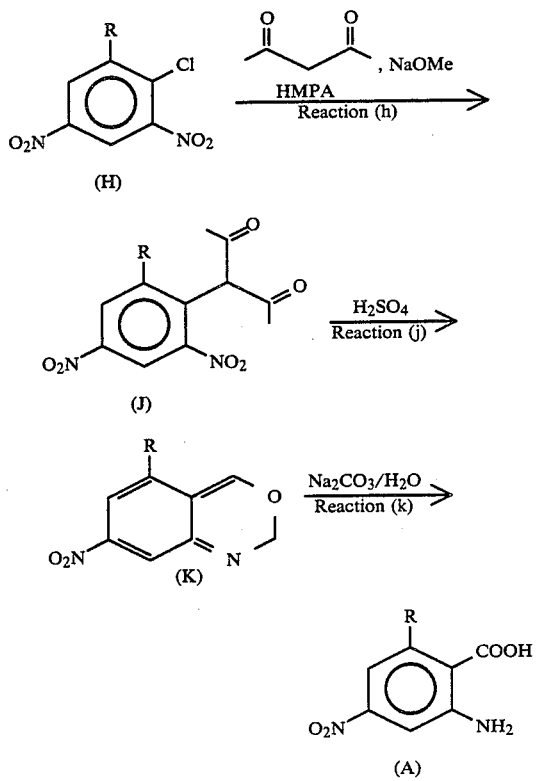

In the reaction (g), the phenol derivative of the formula (G) is converted to a corresponding chloro compound of the formula (H) by the reaction described by Boothroyd et al. (J. CHEM. SOC., pages 1504 to 1508 (1953)).

Next, in the reaction (h), the compound of the formula (H) is reacted with pentane-2,4-dione and sodium methoxide to provide (2-alkyl-4,6-dinitrophenyl)-diacetylmethane of the formula (J) in accordance with a method disclosed by Gambhir et al. (J. Indian Chem. Soc., vol 41, pages 43 to 46 (1964)). Then, in the reaction (j), the compound of the formula (J) is cyclized with concentrated sulfuric acid to form a compound of the formula (K). Finally, in the reaction (k), the compound of the formula (K) is treated with an aqueous solution of sodium carbonate to prepare a 4-nitro-6-alkyl anthranilic acid of the formula (A).

The 4H-3,1-benzoxazin-4-one compound of the formula (I) of the present invention exhibits an inhibitory activity for serine proteases. Particularly, the compound of the formula (I) exhibits a stronger inhibitory activity for elastase, more particularly human leukocyte elastase, than that for other serine proteases, for example, chymotrypsin.

The inhibitory activity of the compound of the present invention against enzyme reaction can be tested in vitro by the following method.

Human purulent sputum elastase is believed to be the same enzyme as human leukocyte elastase, as described by Tomashi et al. (J. BIOL. CHEM., vol. 252, pages 1917 to 1924 (1977)), and can be easily obtained commercially.

As one of the synthetic substrates which has a highly selective activity toward human leukocyte elastase, methoxysuccinyl-L-alanyl-L-alanyl-L-prolyl-L-valylpara-nitroanilide (AAPVpNA) is known (Nakajima et al., J. BIOL. CHEM., vol. 254, pages 4027 to 4032 (1979)), and can be easily obtained commercially.

The extent of the hydrolysis of AAPVpNA by human purulent sputum elastase can be easily determined by measuring the amount of p-nitroaniline released from AAPVpNA, by a spectrophotometer. Then, by comparing the extent of hydrolysis of AAPVpNA by the human purulent sputum elastase in the absence of a compound to be tested with that in the presence of the compound to be tested in various concentrations, a concentration (IC50) of the compound to be tested necessary to inhibit 50% of the elastase reaction can be determined.

An in vitro test similar to that mentioned above can be applied to chymotrypsin.

As a chymotrypsin, α-chymotrypsin of bovine pancreas, which is readily available commercially, is used. As one of the synthetic substrates which has a highly selective activity toward the chymotrypsin, succinyl-L-alanyl-L-alanyl-L-prolyl-L-phenylalanyl-para-nitroanilide (AAPFpNA) is used. The extent of the hydrolysis of AAPFpNA is measured in the absence of a compound to be tested or in the presence of the compound in various concentrations thereof, and thus a concentration (IC50) of the compound necessary to inhibit 50% of the enzyme reaction can be determined.

The specific 4H-3,1-benzoxazin-4-one compounds of the present invention and pharmaceutically acceptable non-toxic salts thereof are useful as an effective component for the serine protease-inhibitory pharmaceutical compositions.

The composition comprises a mixture of a pharmaceutically effective amount of a compound of the formula I or a non-toxic salt thereof and a pharmaceutically acceptable carrier, for example, excipient, solvent or diluent.

In administration, the composition of the present invention may be in a peroral, parenteral, or perrespiratory tract dosage form. The peroral-dosing medicine may be in the form of tablets, pills, pellets, granules, powder, liquid dispersion or capsules. The parenteral dosing medicine may be in the form of an ointment, a cream, and a gel for the skin or under skin. The per respiratory tract-dosing medicine may be in an aerosol dosage form or may be dosed through the respiratory tract by using a suitable atomizing device.

The tablets of the composition of the present invention containing, as a pharmaceutically effective component, the compound of the formula (I) or salts thereof of the present invention can be prepared by mixing the compound or salt of the present invention with an excipient, for example, lactose, starch or crystalline cellulose and, if necessary, a bonding agent, for example, carboxymethyl cellulose, methyl cellulose and polyvinylpyrrolidone and/or a disintegrator, for example, sodium alginate or sodium hydrogen carbonate, and molding or shaping the mixture into the form of tablets by a conventional method.

The liquid or dispersion-form medicines can be prepared by mixing, for example, a glycerol ester or ethyl alcohol with the effective component, and applying a conventional method to the mixture.

The capsule-form medicine can be prepared by mixing granules or a powder or liquid containing the effective component with a capsule-forming material, for example, gelatin and applying a conventional capsule-forming method to the mixture.

An injection liquid can be prepared by dissolving the effective component in a solvent selected in accordance with the form of the liquid, that is, an aqueous or non-aqueous solution, for example, physiological saline, ethyl alcohol, or propylene glycol, and if necessary, by adding an antiseptic and a stabilizer to the solution.

A suppository is used in an ordinary suppository form, for example, gelatin soft capsule containing the effective component.

An ointment or cream can be prepared from the effective component and a necessary carrier by a conventional method.

An aerosol-dosing medicine can be prepared from the effective component, a pharmaceutically acceptable surface active agent produced from, for example, a fatty acid having 6 to 22 carbon atoms, a fatty acid-polyhydric alcohol ester or a cyclic anhydride thereof, and an atomizing agent, for example, alkane having 5 or less carbon atoms or fluorinated alkane.

When a pharmaceutical composition containing the specific 4H-3,1-benzoxazin-4-one compound of the present invention is prescribed for an object to be treated, the dosage is determined in consideration of the condition of a patient and the method of administration of the medicine. Usually, the pharmaceutical composition is preferably prescribed in an amount of 1 to 100 mg of the effective component per adult person per day. Also, the pharmaceutical composition of the present invention is prescribed at once or preferably, periodically 2 to 4 times a day.

The present invention will be further explained by the following examples.

EXAMPLE 1

Preparation of 7-(N-carbobenzoxy-L-prolyl)amino-2-trifluoromethyl-4H-3,1-benzoxazin-4-one In Example 1, the following procedures were carried out.

(A) Synthesis of 4-nitro-N-trifluoroacetyl-anthranilic acid

An amount of 18.2 g of 4-nitroanthranilic acid was dissolved in 50 ml of trifluoroacetic acid, and the resultant solution was cooled to a temperature of 0° C. To the cooled solution, 20 ml of trifluoroacetic anhydride were added dropwise and the mixture stirred for 2 hours while gradually heating to room temperature. The resultant reaction liquid was poured onto ice, and the resultant deposit was collected by filtration, washed with cold water, and then dried. The resultant crude product in an amount of 27 g was recrystallized from ethyl acetate-hexane mixed solvent. The resultant 4-nitro-N-trifluoroacetyl-anthranilic acid was obtained in an amount of 25.1 g and exhibited a melting point of 198° C.

(B) Synthesis of 4-amino-N-trifluoroacetyl-anthranilic acid

An amount of 5.24 g of 4-nitro-N-trifluoroacetyl-anthranilic acid was dissolved in 100 ml of ethyl alcohol, 2 g of a 10% palladium-carbon catalyst were added to the resultant solution, and the resultant mixture was stirred for 2.5 hours at room temperature in a hydrogen gas stream. The resultant reaction mixture was filtered through a Celite filter (trademark, made by Johns Manville Sales), and the catalyst on the Celite filter was washed with ethyl alcohol. The entire amount of the filtrate was collected, concentrated, and dry solidified under a reduced pressure, and the resultant crude product in an amount of 4.7 g was recrystallized from an ethyl alcohol-hexane or ethyl alcohol-water mixed solvent.

The resultant 4-amino-N-trifluoroacetylanthranilic acid was collected in an amount of 4.25 g and exhibited a melting point of 228° C.

(C) Synthesis of 4-(N-carbobenzoxy-L-prolyl)amino-N-trifluoroacetyl-anthranilic acid A solution was prepared by dissolving 249 mg of N-carbobenzoxy-L-proline and 101.2 mg of N-methylmorpholine in 5 ml of dried tetrahydrofuran, and the resultant solution was cooled to a temperature of −15° C. The solution was mixed with 136.6 mg of isobutyl chloroformate, the resultant mixture was stirred for 2 minutes at a temperature of −15° C. to −10° C., and a solution of 250 mg of 4-amino-N-trifluoroacetyl-antranilic acid and 101.2 mg of N-methylmorpholine in 2 ml of dried tetrahydrofuran was then added dropwise to the mixture. The resultant reaction mixture was stirred for one hour at a temperature of −15° C. to −10° C., was gradually heated to room temperature, and was then stirred for 18 hours at room temperature. The resultant deposit was removed by filtration, the filtrate was concentrated under a reduced pressure, and an oily product was obtained. The oily product was dissolved in ethyl acetate, and the resultant solution was washed with a saturated brine. The resultant ethyl acetate layer was dried with anhydrous sodium sulfate, and was concentrated under a reduced pressure to provide 240 mg of a light yellow oily product. This crude oily product was purified by a silica gel column chromatography. The purified oily 4-(N-carbobenzoxy-L-prolyl)amino-N-trifluoroacetyl-anthranilic acid was obtained in an amount of 110 mg.

(D) Synthesis of 7-(N-carbobenzoxy-L-prolyl)amino-2-trifluoromethyl-4H-3,1-benzoxazin-4-one A solution was prepared by dissolving 100 mg of 4-(N-carbobenzoxy-L-prolyl)amino-N-trifluoroacetyl-anthranilic acid in 1 ml of dry ethyl acetate and cooled to a temperature of 0° C. The solution was mixed with 49 mg of N,N'-dicyclohexylcarbodiimide and the resultant mixture was stirred at a temperature of 4° C. for 18 hours. The resultant deposit consisting of N,N'-dicyclohexylurea and separated from the mixture was removed by filtration.

The filtrate was concentrated under a reduced pressure, and a light yellow oily substance was obtained in an amount of 90 mg. This crude oily substance was purified by a silica gel column chromatography and was recrystallized from an ethyl acetate-hexane mixed solvent. The purified 7-(N-carbobenzoxy-L-prolyl)amino-2-trifluoromethyl-4H-3,1-benzoxazin-4-one was obtained in an amount of 12 mg and exhibited a melting point of 68° to 70° C.

$^1$H - NMR (CDCl$_3$, δ ppm)
1.8–2.1 (4H, m) 3.35–3.65 (2H, m)
5.15–5.3 (1H, m) 5.23 (2H, s)
7.39 (5H, s) 7.2–7.6 (2H, m)
8.14 (1H, d, J=8.8 Hz)
8.6–8.7 (1H, m)

Other 7-(N-A-Y)amino-2-trifluoro methyl-4H-3,1-benzoxazin-4-one compounds shown in Table 1 can be prepared by the same method as that described above, except that in the above-mentioned step (C), N-carbobenzoxy-L-proline was replaced by the N-carbobenzoxy-amino acids corresponding to the (N—A—Y) radicals shown in Table 1.

TABLE 1

| 7-(N-A-Y)amino-2-trifluoromethyl-4H-3,1-benzoxazin-4-one compound |
|---|
| 7-(N-A-Y)radical |
| 7-(N-carbobenzoxy-L-alanyl) |
| 7-(N-carbobenzoxy-glycyl) |
| 7-(N-carbobenzoxy-L-isoleucyl) |
| 7-(N-carbobenzoxy-L-leucyl) |
| 7-(N-carbobenzoxy-L-phenylalanyl) |
| 7-(N-carbobenzoxy-L-valyl) |
| 7-(N-carbobenzoxy-L-norvalyl) |
| 7-(N-carbobenzoxy-L-norleucyl) |
| 7-(N-carbobenzoxy-L-phenylglycyl) |
| 7-(N-α,N-ε-dicarbobenzoxy-L-lysyl) |
| 7-(N-carbobenzoxy-L-aspartyl) |
| 7-(N-carbobenzoxy-L-glutamyl) |

EXAMPLES 2 TO 14

Preparation of 7-(N-A-Y)amino-2-isopropoxy-4H-3,1-benzoazin-4-one compounds

In Example 2, the following procedures were carried out.

(A) Synthesis of 2-carboisopropoxyamino-4-nitrobenzoic acid

A solution was prepared by dissolving 41.23 g of 4-nitro anthoanilic acid and 25.30 g of N-methylmorpholine in 600 ml of dry tetrahydrofuran and cooling to a temperature of −10° C. The solution was mixed with 30.65 g of isopropyl chloroformate and the mixture was cooled to a temperature of −10° C. The resultant reaction mixture was stirred at a temperature of 10° C. for 2 hours and then at room temperature for 60 hours. The resultant deposit formed in the reaction mixture was removed by filtration, the filtrate was concentrated and dried under a reduced pressure, and the resultant crude product was recrystallized from an ethylacetate-hexane mixed solvent. The resultant 2-carboisopropoxyamino-4-nitrobenzoic acid was obtained in an amount of 55.1 g and had a melting point of 231° C.

(B) Synthesis of 4-amino-2-carboisopropoxyaminobenzoic acid

A solution was prepared by dissolving 13.08 g of 2-carboisopropoxyamino-4-nitrobenzoic acid in 200 ml of ethyl alcohol and was mixed with 3 g of a 10% palladium-carbon catalyst. The resultant reaction mixture was stirred at room temperature in a hydrogen gas atmosphere for 2 hours. Then, the reaction mixture was filtered through a Celite filter and the catalyst on the Celite filter was washed with ethyl alcohol. The entire amount of the filtrate was collected, concentrated and dried under a reduced pressure, and the resultant crude product was recrystallized from an ethyl alcohol-water mixed solvent. The resultant 4-amino-2-carboisopropoxyaminobenzoic acid was obtained in a yield of 11.3 g and exhibited a melting point of 197° C.

(C) Synthesis of 2-carboisopropoxyamino-4-(N-carbobenzoxy-L-prolyl)aminobenzoic acid A solution was prepared by dissolving 249 mg of N-carbobenzoxy-L-proline and 101.0 mg of N-methylmorpholine in 5 ml of dry tetrahydrofuran and cooling to a temperature of −15° C. The solution was mixed with 136.6 mg of isobutyl chloroformate and the mixture was stirred at a temperature of −15° C. to −10° C. for 2 minutes. Then, a solution of 238 mg of 4-amino-2-carboisopropoxyaminobenzoic acid and 101.2 mg of N-methylmorpholine in 2 ml of dry tetrahydrofuran was added dropwise to the above-mentioned mixture. The resultant reaction mixture was stirred at a temperature of −15° C. to −10° C. for one hour, gradually heated to room temperature, and then stirred at room temperature for 18 hours. The resultant deposit generated in the reaction mixture was removed by filtration, the filtrate was concentrated under a reduced pressure, and an oily yellow substance was obtained.

The oily substance as dissolved in ethyl acetate, the solution was washed with a 1N-hyrochloric acid and a saturated brine, and the resultant ethyl acetate fraction was dried with anhydrous sodium sulfate, concentrated under a reduced pressure, and a light yellow oily substance was obtained in an amount of 680 mg.

The oily substance was purified by a silica gel column chromatography. The resultant purified 2-carboisopropoxyamino-4-(N-carbobenzoxy-L-prolyl)aminobenzoic acid in an amount of 125 mg exhibited a melting point of 115° C.

(D) Synthesis of 7-(N-carbobenzoxy-L-orolyl)amino-2-isopropoxy-4H-3,1-benzoxazin-4-one compound A solution was prepared by dissolving 82 mg of 2-carboisopropoxyamino-4-(N-carbobenzoxy-L-prolyl)aminobenzoic acid in 1 ml of dry ethyl acetate and chilling to a temperature of 0° C. The solution was mixed with 40 mg of N,N,-dicyclohexylcarbodiimide, and the resultant reaction mixture was heated to room temperature and was stirred for 18 hours. The resultant deposit consisting of N,N'-dicyclohexylurea was removed by filtration and the remaining filtrate was concentrated under a reduced pressure to provide 100 mg of a light yellow crude oily substance. The crude oily substance was purified by a silica gel column chromatography and then recrystallized from an ethyl acetate-hexane mixed solvent.

A purified 7-(N-carbobenzoxy-L-prolyl)amino-2-isopropoxy-4H-3,1-benzoxazin-4-one was obtained in a yield of 22 mg and exhibited a melting point of 84° C.

$^1$H - NMR (CDCl$_3$, δppm)
1.43 (6H, d, J=6.1 Hz) 1.8–2.1 (4H, m)
3.4–3.6 (2H, m) 4.4–4.6 (1H, m)
5.2–5.35 (1H, m) 5.23 (2H, s)
7.2–7.4 (6H, m) 7.7 (1H, m)
8.00 (1H, d, J=8.8 Hz) 9.7–9.85 (1H, m)

In each of Examples 3 to 14, the same procedures as those described in Example 2 were carried out, with the following exception.

In the above-described step (C), an amino acid having a protective radical, such as an N-carbobenzoxy amino acid, N-acetylamino acid or N-tert-butoxycarbonyl amino acid compound as shown in Table 2, was used in place of the N-carbobenzoxy-L-proline. The resultant 4-(N-A-Y)amino-2-carboisopropoxyamino benzoic acid was directly subjected to the next step (D) without purification.

TABLE 2

| Example No. | Amino radical-protected amino acid |
|---|---|
| 1 | |
| 3 | N-carbobenzoxy-L-alanine |
| 4 | N-carbobenzoxy-L-valine |
| 5 | N-carbobenzoxy-L-phenylalanine |
| 6 | N-α,N-ε-dicarbobenzoxy-L-lysine |
| 7 | N-carbobenzoxy-L-glutamic acid(γ-benzyl-ester) |
| 8 | N-carbobenzoxy-D-phenylalanine |
| 9 | N-tert-butoxycarbonyl-L-phenylalanine |
| 10 | N-tert-butoxycarbonyl-L-proline |
| 11 | N-acetyl-L-proline |
| 12 | N-carbobenzoxy-L-alanyl-L-proline |
| 13 | N-carbobenzoxy-L-prolyl-L-valine |
| 14 | N-carbobenzoxy-L-phenylalanyl-L-valine |

Also, in the above-described step (D), a 2-carboisopropoxyamino-4-(N-A-Y)amino benzoic acid obtained from the amino radical-protected amino acid compound shown in Table 2 was used in place of 2-carboisopropoxyamino-4-(N-carbobenzoxy-L-prolyl)amino benzoic acid.

The type of 7-(N-A-Y) radical and the melting point of the resultant 7-(N-A-Y)amino-2-isopropoxy-4H-3,1-benzoxazin-4-one compound are shown in Table 3.

TABLE 3

| | 7-(N-A-Y)amino-2-isopropoxy-4H-3,1-benzoxazin-4-one compound | |
|---|---|---|
| Example No. | N-(N-A-Y)radical | Melting point (°C.) |
| 2 | 7-(N-carbobenzoxy-L-prolyl) | 84 |
| 3 | 7-(N-carbobenzoxy-L-alanyl) | 147 to 149 |
| 4 | 7-(N-carbobenzoxy-valyl) | 191 to 192 |
| 5 | 7-(N-carbobenzoxy-L-phenylalanyl) | 181 |
| 6 | 7-(N-α,N-ε-dicarbobenzoxy-L-lysyl) | 119 |
| 7 | 7-(N-carbobenzoxy-L-glutamyl) | 136 (benzyl ester) |
| 8 | 7-(N-carbobenzoxy-D-phenylalanyl) | 183 |
| 9 | 7-(N-tert-butoxycarbonyl-L-phenylalanyl) | 102 |
| 10 | 7-(N-tert-butoxycarbonyl-L-prolyl) | 138 to 139 |
| 11 | 7-(N-acetyl-L-prolyl) | 168 to 170 |
| 12 | 7-(N-carbobenzoxy-L-alanyl-L-prolyl) | 112 to 114 |
| 13 | 7-(N-carbobenzoxy-L-prolyl-L-valyl) | 107 |
| 14 | 7-(N-carbobenzoxy-L-phenylalanyl-L-valyl) | 196 |

Other 7-(N-A-Y)amino-2-isopropoxy-4H-3,1-benzoxazin-4-one compounds as indicated in Table 4 can be prepared by the same procedures as described above, except that in the above-mentioned step (C), the N-carbobenzoxyproline is replaced by the amino acid compounds corresponding to the (N-A-Y) radicals indicated in Table 4.

TABLE 4

| 7-(N-A-Y)amino-2-isopropoxy-4H-3,1-benzoxazin-4-one compound |
|---|
| 7-(N-A-Y)radical |
| 7-(N-carbobenzoxyglycyl) |
| 7-(N-carbobenzoxy-L-isoleucyl) |
| 7-(N-carbobenzoxy-L-leucyl) |
| 7-(N-carbobenzoxy-L-norvalyl) |
| 7-(N-carbobenzoxy-L-norleucyl) |
| 7-(N-carbobenzoxy-L-phenylglycyl) |
| 7-(N-carbobenzoxy-L-aspartyl) |

EXAMPLE 15

Preparation of 7-(N-carbobenzoxy-L-phenylalanyl)amino-2-isopropoxy-5-methyl-4H-3,1-benzoxazin-4-one compounds In Example 15, the following procedures were carried out.

(A) Synthesis of 2-carboisopropoxyamino-6-methyl-4-nitro benzoic acid

A solution was prepared by dissolving 5.3 g of 6-methyl-4-nitroantranilic acid and 3.1 g of N-methylmorpholine in 20 ml of dry tetrahydrofuran and chilling to a temperature of −10° C. The solution was mixed with 3.7 g of isopropyl chloroformate and the resultant reaction mixture was stirred at a temperature of −10° C. for 2 hours and then at room temperature for 60 minutes.

The resultant deposit in the reaction mixture was removed by filtration and the remaining filtrate was concentrated and dried under a reduced pressure. The resultant crude product was recrystallized from an ethyl acetate-hexane mixed solvent.

A purified 2-carboisopropoxyamino-6-methyl-4-nitro benzoic acid was obtained in a yield of 5.3 g.

(B) Synthesis of 4-amino-2-carboisopropoxyamino-6-methyl benzoic acid

A reaction mixture was prepared by dissolving 5.3 g of 2-carboisopropoxyamino-6-methyl-4-nitro benzoic acid in 100 ml of ethyl alcohol and then mixing the solution with 1 g of a 10% palladium-carbon catalyst. The reaction mixture was stirred at room temperature in a hydrogen gas atmosphere for 2 hours, and the resultant mixture was filtered through a Celite filter and the catalyst on the Celite filter was washed with ethyl alcohol. The entire filtrate was collected, concentrated, and dried under a reduced pressure, and the resultant crude product was recrystallized from an ethyl acetate-hexane mixed solvent.

4-amino-2-carboisopropoxyamino-6-methyl benzoic acid was obtained in an amount of 4.05 g.

(C) Synthesis of 2-carboisopropoxyamino-4-(N-carbobenzoxy-L-phenylalanyl) amino-6-methyl benzoic acid A solution was prepared by dissolving 599 mg of N-carbobenzoxy-L-phenylalanine and 202.4 mg of N-methylmorpholine in 2 ml of dry tetra-hydrofuran and chilled to a temperature of −15° C. The solution was mixed with 273.2 mg of isobutyl chloroformate and the resultant mixture was stirred at a temperature of −15° C. to −10° C. for 2 minutes. Then, a solution of 505 mg of 4-amino-2-carboisopropoxyamino-6-methyl benzoic acid and 202.4 mg of N-methylmorpholine in 2 ml of dry tetrahydrofuran was added dropwise to the mixture, the resultant reaction mixture was stirred at a temperature of −15° C. to −10° C. for one hour, was gradually heated to room temperature, and was further stirred at room temperature for 18 hours. The resultant deposit formed in the reaction mixture was removed by filtration and the remaining filtrate was concentrated under a reduced pressure to provide a yellow oily substance. This oily substance was dissolved in ethyl acetate and the resultant solution was washed with an 1N-hydrochloric acid and then with a saturated brine. The resultant ethyl acetate layer was dried with anhydrous sodium sulfate, and was concentrated under a reduced pressure to provide 683 mg of a light yellow oily substance. The crude oily substance was purified by a silica gel column chromatography.

2-carboisopropoxyamino-4-(N-carbobenzoxy-L-phenylalanyl) amino-6-methyl benzoic acid was obtained in an amount of 273 mg.

(D) Synthesis of 7(N-carbobenzoxy-L-phenylalanyl)amino-2-isopropoxy-5-methyl-4H-3,1-benzoxazin-4-one A solution prepared by dissolving 267 mg of 2-carboisopropoxyamino-4-(N-carbobenzoxy-L-phenyl- alanyl)amino-5-methyl benzoic acid in 2 ml of dry tetrahydrofuran was chilled to a temperature of 0° C. The solution was mixed with 113.5 mg of N,N'-dicyclohexylcarbodiimide and the resultant mixture was gradually heated to room temperature and the stirred for 18 hours. The resultant deposit consisting of N,N'-dicyclohexylurea was removed by filtration and the remaining filtrate was concentrated under a reduced pressure to provide 300 mmg of a light yellow oily substance. This crude oily substance was purified by a silica gel column chromatography and then recrystallized from an ethyl acetate-hexane mixed solvent.

7-(N-carbobenzoxy-L-phenylalanyl)amino-2-isopropoxy-5-methyl-4H-3,1-benzoxazin-4-one was obtained in an amount of 120 mg.

m. p. : 137° C.

$^1$H - NMR (CDCl$_3$, δppm)
1.41 (6H, d, J=6.2 Hz) 2.66 (3H, s)
3.16 (2H, d, J=7.0 Hz) 4.45–4.75 ( 1H, m)
5.12 (2H, m) 5.2–5.5 (2H, m)
6.9–7.0 (1H, m) 7.32 (10H, s)
7.44 (1H, d, J=2.0 Hz) 7.95–8.1 (1H, m)

IR (KBr, cm$^{-1}$):
3300, 1760, 1680, 1640, 1595, 1535, 1305, 905

The 7-(N-A-Y)amino-2-isopropoxy-5-methyl-4H-3,1-benzoxazin-4-one compounds as indicated in Table 5 can be prepared by the same procedures as described above, except that in the above-mentioned step (C), the N-carbobenzoxy-L-phenylalanine is replaced by an amino radical-protected amino acids such as N-carbobenzoxy amino acids, N-tert-butoxycarbonyl amino acids, and N-acetyl amino acids, corresponding to the (N-A-Y)radicals indicated in Table 5.

TABLE 5

| 7-(N-A-Y)amino-2-isopropoxy-5-methyl-4H-3,1-benzoxazin-4-one compound |
|---|
| 7-(N-A-Y)radical |
| 7-(N-carbobenzoxy-L-alanyl) |
| 7-(N-carbobenzoxy-glycyl) |
| 7-(N-carbobenzoxy-L-isoleucyl) |
| 7-(N-carbobenzoxy-L-leucyl) |
| 7-(N-carbobenzoxy-L-prolyl) |
| 7-(N-carbobenzoxy-L-valyl) |
| 7-(N-carbobenzoxy-L-norvalyl) |
| 7-(N-carbobenzoxy-L-norleucyl) |
| 7-(N-carbobenzoxy-L-phenylglycyl) |
| 7-(N-α,N-ε-dicarbobenzoxy-L-lysyl) |
| 7-(N-carbobenzoxy-L-aspartyl) |
| 7-(N-carbobenzoxy-L-glutamyl) |
| 7-(N-carbobenzoxy-D-phenylalanyl |
| 7-(N-tert-butoxycarbonyl-L-phenylalanyl) |
| 7-(N-tert-butoxycarbonyl-L-prolyl) |
| 7-(N-acetyl-L-prolyl) |
| 7-(N-carbobenzoxy-L-alanyl-L-prolyl) |
| 7-(N-carbobenzoxy-L-prolyl-L-valyl) |
| 7-(N-carbobenzoxy-L-phenylalanyl-L-valyl) |

EXAMPLE 16

Preparation of 7-(N-carbobenzoxy-L-phenyalanyl)amino-2-isopropylamino-4H-3,1-benzoxazin-4-one compound In Example 16, the following procedures were carried out.

(A) Synthesis of methyl 2-(3-isopropylureido)-4-nitro benzoate

A reaction mixture was prepared by dissolving 5.4 g of 4-nitro anthranilic acid in 50 ml of dry tetrahydrofuran, and by adding 4.09 g of isopropyl isocyanate to the solution. The reaction mixture was heated while refluxing in a nitrogen gas atmosphere for 5 hours, and the resultant reaction mixture was concentrated under a reduced pressure. The resultant crude 2-(3-isopropylureido)-4-nitro benzoic acid was dissolved in a tetrahyirofuran-acetone mixed solvent, and the resultant solution chilled to a temperature of 0° C. To this solution, a solution of diazomethane in ether was gradually added. After completion of the reaction was confirmed by a TLC, the solvent was removed and the resultant residue was purified by a silica gel column chromatography. Methyl 2-(3-isopropylureido)-4-nitro benzoate was obtained in an amount of 2.13 g.

m.p.: 201 to 203° C. (hexane-ethyl acetate)

$^1$H-NMR (CDC13, δppm):
1.24 (6H, d, J=6.4 Hz), 3.97 (3H, s), 3.8–
4.1 (1H,m)4.4–4.7 (1H, m) 7.71 (1H, dd,
J =8.8, 2.2 Hz), 8.12 (lH, d, J =8.8 Hz),
9.47 (1H, d, J=2.2 Hz), 10.32 (1H, br d)

IR(KBr, cm$^{-1}$):
3325, 2980, 1715, 1650, 1560, 1540, 1430, 1350, 1260

(B) Synthesis of methyl 2-(3-isoprooylureido)-4-amino benzoate

A solution of 99 mg of methyl 2-(3-isopropylureido)-4-nitro benzoate in 20 ml of ethyl acetate was mixed with 60 mg of a 10% Pd-C catalyst, and the resultant reaction mixture was stirred at room temperature in a hydrogen gas atmosphere for one hour. Thereafter, the reaction mixture was filtered to remove the catalyst, and the filtrate was concentrated under a reduced pressure. The resultant crude product was purified by a silica gel column chromatography. Methyl 2-(3-isopropylureido)-4-amino benzoate was obtained in an amount of 81 mg.

$^1$H-NMR (CDCl$_3$, δppm):
1.19 (6H, d, J=6.4 Hz), 3.82 (3H, s),
3.7–4.3 (3H, m), 4.4–4.7 (1H, m),
6.19 (1H, dd, J=8.8, 2.4 Hz), 7.77 (1H,
d, J=8.8 Hz), 7.87 (1H, d, J=2.4 Hz),
10.47 (1H, br s)

IR (KBr, cm$^{-1}$): 3450, 3310, 1695, 1655, 1615, 1580, 1550, 1260

(C) Synthesis of 2-isopropylamino-7-amino-4H-3,1-benzoxazin-4-one

A solution prepared by dissolving 98 mg of methyl 2-(3-isopropylureido)-4-amino benzoate in 1 ml of a concentrated sulfuric acid was stirred at room temperature for one hour. The solution was gradually added dropwise to a solution of 2 g of sodium hydrogen carbonate in 5 ml of ethyl acetate and 5 ml of water while the mixture was stirred and chilled with ice. The reaction mixture was neutralized by further adding sodium hydrogen carbonate and then extracted with ethyl acetate. The resultant organic layer was washed with a saturated brine and then dried with anhydrous magnesium sulfate. This organic phase was concentrated under a reduced pressure, and the resultant crude product was purified by a silica gel column chromatography. The refined 2-isopropylamino-7-amino-4H-3,1-benzoxazin-4-one was obtained in an amount of 47 mg.

$^1$H-NMR (d5-pyridine, δppm): 1.26 (6H, d, J=6.4 Hz), 4.0–4.5 (1H,°
br, m), 6.5–6.8 (2H, br s), 6.74 (1H, dd, J=8.6, 2.2 Hz), 6.90 (1H, d, J=
2.2 Hz), 8.09 (1H, d, J=8.6 Hz),
8.25–8.5 (1H, m)

(D) Synthesis of 7-(N-carbobenzoxy-L-pohenylalanyl)amino-2-isopropylamino-4H-3,1-benzoxazin-4-one A solution prepared by dissolving 126 mg of N-carbobenzoxy-L-phenylalanine and 35 µl of N-methylmorpholine in 1 ml of dry tetrahydrofuran was chilled to a temperature of −17° C. in a nitrogen gas stream. The solution was mixed with 57 µl of isobutyl chloroformate, the resultant mixture was stirred at a temperature of −17° C. for 3 minutes, and then a solution of 92 mg of 2-isopropylamino-7-amino-4H-3,1-benzoxazin-4-one and 46 µl of methylmorpholine in 3.5 ml of dry tetrahydrofuran was gradually added dropwise to the mixture. The resultant reaction mixture was stirred at a temperature of −17° C. to −10° C. for one hour, gradually heated to room temperature, and then further stirred at room temperature for 18 hours. The resultant deposit was removed from the reaction mixture by filtration and filtrate was mixed with ethyl acetate, and washed successively with a 1N-hydrochloric acid, with a saturated sodium hydrogen carborate aqueous solution, and with a saturated brine. The resultant organic fraction of the mixture was dried with anhydrous magnesium sulfate and then concentrated under a reduced pressure. The resultant crude product as purified with a silica gel column chromatography. A final product consisting of 7-(N-carbobenzoxy-L-phenylalanyl)amino-2-isopropylamino-4H-3,1-benzoxazin-4-one was obtained in an amount of 70 mg.

m.p.: 176°–179° C. (n-hexane-ethyl acetate) $^1$H-NMR (CDCl$_3$, δ ppm): 1.27 (6H, d, J=6.4 Hz), 3.17 (2H, d, J =7.0 Hz), 3.85–4.30 (1H, m), 4.3–4.8
(2H, m), 5.12 (2H, s), 5.34 (1H, br d,
J=7.5 Hz), 7.05 (1H, dd, J=2.0,
8.6 Hz), 7.25 [5H, s), 7.32 (5H, s), 7.40
(1H, d, J=2.0 Hz), 7.90 (1H, d,
J=8.6 Hz), 7.75–7.9 (1H, br s) IR (KBr, cm$^{-1}$): 3430, 3210, 2950, 1740, 1615, 1585, 1540, 1275 FD-MS (m/z): 500 (M+) EI-MS (m/z): 500 (M+)392, 334, 281, 187, 131, 91.

Other 7-(N-A-Y)amino-2-isopropylamino-4H-3,1-benzoxazine-4-one compounds indicated in Table 6 can be produced by the same procedures as mentioned above, except that in the above-mentioned step (D), the N-carbobenzoxy-L-phenylalanine is replaced by a N-carbobenzoxy amino acid corresponding to the 7-(N-A-Y) radical indicated in Table 6.

TABLE 6

| 7-(N-A-Y)amino-2-isopropylamino-4H-3,1-benzoxazin-4-one Compound |
|---|
| 7-(N-A-Y)radical |
| 7-(N-carbobenzoxy-L-phenylalanyl) |

TABLE 6-continued

| 7-(N-A-Y)amino-2-isopropylamino-4H-3,1-benzoxazin-4-one Compound |
|---|
| 7-(N-A-Y)radical |
| 7-(N-carbobenzoxy-L-alanyl) |
| 7-(N-carbobenzoxyglycyl) |
| 7-(N-carbobenzoxy-L-isoleucyl) |
| 7-(N-carbobenzoxy-L-leucyl) |
| 7-(N-carbobenzoxy-L-prolyl) |
| 7-(N-carbobenzoxy-L-valyl) |
| 7-(N-carbobenzoxy-L-norvalyl) |
| 7-(N-carbobenzoxy-L-norleucyl) |
| 7-(N-carbobenzoxy-L-phenylglycyl) |
| 7-(N-α,N-ε-dicarbobenzoxy-L-lysyl) |
| 7-(N-carbobenzoxy-L-aspartyl) |
| 7-(N-carbobenzoxy-L-glutamyl) |

EXAMPLE 17

Preparation of 7-(N-carbobenzoxy-L-phenylalanyl)amino-5-methyl-2-isoorooylamino-4H-3,1- benzoxazin-4-one compound In Example 17, the following procedures were carried out.

(A) Synthesis of methyl 2-(3-isocrocylureido)-4-nitro-6-methyl benzoate

A reaction mixture was prepared by dissolving 1.0 g of 4-nitro-6-methyl anthranilic acid in 10 ml of dry tetrahydrofuran, and by adding 1.3 g of isopropyl isocyanate to the solution. The reaction mixture was heated while refluxing in a nitrogen gas atmosphere for 20 hours, and the resultant reaction mixture was concentrated under a reduced pressure. The resultant crude 2-(3-isopropylureido)-4-nitro-6-methyl benzoic acid was dissolved in a tetrahyirofuran-methyl alcohol mixed solvent, and the resultant solution was chilled to a temperature of 0° C. To this solution, a solution of diazomethane in ether was gradually added. After completion of the reaction was confirmed by a TLC, the solvent was removed and the resultant residue was purified by a silica gel column chromatography. Methyl 2-(3-isopropylureido)-4-nitro-6-methyl benzoate was obtained in an amount of 0.36 g.

$^1$H-NMR (CDCl$_3$, δ ppm): 1.23 (6H, d, J=6.4 Hz), 2.53 (3H, s), 3.98 (3H, s), 3.75–4.15 (1H, m), 4.3 –4.55 (1H, m), 7.66 (1H, d, J=2.0 Hz), 8.7–8.85 (1H, m), 9.03 (1H, d, J=2.0 Hz)

(B) Synthesis of methyl 2-(3-isopropylureido)-4-amino-6-methyl benzoate

A solution of 98 mg of methyl 2-(3-isopropylureido)-4-nitro-6-methyl benzoate in 30 ml of ethyl acetate was mixed with 40 mg of a 10% Pd-C catalyst, and the resultant reaction mixture was stirred at room temperature in a hydrogen gas atmosphere for 4 hours. Thereafter, the reaction mixture was filtered to remove the catalyst, and the filtrate was concentrated under a reduced pressure. The resultant crude product was purified by a silica gel column chromatography. Methyl 2-(3-isopropylureido)-4-amino-6-methyl benzoate was obtained in an amount of 86 mg. $^1$H-NMR (CDCl$_3$, δ ppm): 1.18 (6H, d, J=6.4 Hz), 2.38 (3H, s), 3.83 (3H, s), 3.7–4.2 (3H, m), 4.4 4.65 (1H, m), 6.10 (1H, d, J=2.4 Hz), 7.65 (1H, d, J=2.4 Hz), 9.8–10.1 (1H, m)

(C) Synthesis of 2-isopropylamino-5-methyl-7-amino-4H-3,1-benzoxazin-4-one

A solution prepared by dissolving 73 mg of methyl 2-(3-isopropylureido)-4-amino-6-methyl benzoate in 1 ml of a concentrated sulfuric acid was stirred at room temperature for one hour. The solution was gradually added dropwise to a solution of 4 g of sodium hydrogen carbonate in 5 ml of ethyl acetate and 5 ml of water while the mixture was stirred and chilled with ice. The reaction mixture was neutralized by further adding sodium hydrogen carbonate and then extracted with ethyl acetate. The resultant organic layer was washed with a saturated brine and then dried with anhydrous magnesium sulfate. This organic phase was concentrated under a reduced pressure, ant the resultant crude product was purified by a silica gel column chromatography. The refined 2-isopropylamino-5-methyl-7-amino-4H-3,1-benzoxazin-4-one was obtained in an amount of 62 mg. $^1$H-NMR (d5-pyridine, δ ppm):

1.24 (6H, d, J=6.4 Hz), 2.75 (3H, m),
4.0–4.4 (1H, br, m), 6.2–6.6 (3H, br s), 6.65–6.8 (1H, br s), 8.0–8.3 (1H, m)

(D) Synthesis of 7-(N-carbobenzoxy-L-phenylalanyl)amino-5-methyl-2-isopropylamino-4H-3,1-benzoxazin4-one A solution prepared by dissolving 96 mg of N-carbobenzoxy-L-phenylalanine and 35 μl of N-methylmorpholine in 1 ml of dry tetrahydrofuran was chilled to a temperature of −17° C. in a nitrogen gas stream. The solution was mixed with 44 μl of isobutyl chloroformate, the resultant mixture was stirred at a temperature of −17° C. for 3 minutes, and then a solution of 75 mg of 2-isopropylamino-5-methyl-7-amino-4H-3,1-benzoxazin-4one and 35 μl of N-methylmorpholine in 3 ml of dry tetrahydrofuran was gradually added dropwise to the mixture. The resultant reaction mixture was stirred at a temperature of −17° C. to −10° C. for one hour, gradually heated to room temperature, and then further stirred at room temperature for 18 hours. The resultant deposit was removed from the reaction mixture by filtration and filtrate was mixed with ethyl acetate, and washed successively with a 1N-hydrochloric acid, with a saturated sodium hydrogen carbonate aqueous solution, and with a saturated brine. The resultant organic fraction of the mixture was dried with anhydrous magnesium sulfate and then concentrated under a reduced pressure. The resultant crude product was purified with a silica gel column chromatography. A final product consisting of 7-(N-carbobenzoxy-L-phenylalanyl)amino-5-methyl-2-isopropylamino-4H-3,1-benzoxazin-4-one was obtained in an amount of 70 mg.

m.p.: 200°–202° C. (n-hexane-ethyl acetate)
$^1$H-NMR (CDCl$_3$, δ ppm): 1.26 (6H, d, J=6.4 Hz), 2.64 (3H, s), 3.15 (2H, d, J=6.8 Hz), 3.9–4.2 (1H, m), 4.4–4.7 (1H, m), 4.8–5.0 (1H, m), 5.11 (2H, s), 5.3–5.5 (1H, m), 6.89 (1H, d, J=2.0 Hz), 7.32 (11H, s), 7.8–8.2 (1H, m) FD-MS (m/z): 514 (M+)

Other 7-(N-A-Y)amino-5-methyl-2-isopropylamino-4H-3,1- benzoxazin-4-one compounds as indicated in Table 7 can be produced by the same procedures as described above, except that in the above-mentioned step (D), the N-carbobenzoxy-L-phenylalanine is replaced by N-carbobenzoxy amino acids co:.responding to the 7-(N-A-) radicals indicated in Table 7.

TABLE 7

| 7-(N-A-Y)amino-5-methyl-2-isopropylamino-4H-3,1-benzoxazin-4-one Compound |
|---|
| 7-(N-A-Y)radical |
| 7-(N-carbobenzoxy-L-alanyl) |
| 7-(N-carbobenzoxyglycyl) |
| 7-(N-carbobenzoxy-L-isoleucyl) |
| 7-(N-carbobenzoxy-L-leucyl) |

TABLE 7-continued 7-(N-A-Y)amino-5-methyl-2-isopropylamino-
4H-3,1-benzoxazin-4-one Compound 7-(N-A-Y)radical 7-(N-carbobenzoxy-L-prolyl)
7-(N-carbobenzoxy-L-valyl)
7-(N-carbobenzoxy-L-norvalyl)
7-(N-carbobenzoxy-L-norleucyl)
7-(N-carbobenzoxy-L-phenyl-glycyl)
7-(N-α,N-ε-dicarbobenzoxy-L-lysyl)
7-(N-carbobenzoxy-L-aspartyl)
7-(N-carbobenzoxy-L-glutamyl)

EXAMPLE 18

Preparation of 7-(N-carbobenzoxy-L-phenylalanyl)amino-2-methyl-4H3,1-benzoxazin-4-one Compounds In Example 18, the following procedures were carried out.

(A) Synthesis of 4-nitro-N-acetyl-anthranilic acid

A solution prepared by dissolving 1 42 g of 4-nitro anthranilic acid in 5 ml of acetic anhydride was heated and stirred at a temperature of 140° C. for 2 hours. The resultant reaction solution was poured onto ice. The resultant deposit was collected by filtration, washed with cold water and then dried. A crude product containing 7-nitro-2-methyl-4H-3,1-benzoxazin-4-one was obtained in an amount of 1.51 g. A portion (829 mg) of the crude product was dissolved in 5 ml of tetrahydrofuran, the resultant solution was mixed with 2 ml of an 1N-sodium hydroxide aqueous solution, and the reaction mixture was heated for 1.5 hours while refluxing. The reaction mixture was acidified with an 1N-hydrochroric acid and extracted with ethyl acetate. The resultant organic phase was washed with a saturated brine, and dried with anhydrors magnesium sulfate. The organic phase was concentrated under a reduced pressure.

A final product consisting of 4-nitro-N-acetyl anthranilic acid was obtained in an amount of 890 mg.

(B) Synthesis of 4-amino-N-acetyl-anthranilic acid

A reaction mixture prepared by dissolving 575 mg of 4-nitro-N-acetyl-anthranilic acid in 200 ml of ethyl acetate and by mixing the resultant solution with 100 mg of a 10% Pd-C catalyst was stirred at room temperature in a hydrogen gas atmosphere for 4 hours. Then, the reaction mixture was filtered through a Celite filter to remove the catalyst, and the catalyst was washed with ethyl acetate. The total amount of the filtrate was collected and concentrated under a reduced a silica gel column chromatography. A final product consisting of 4-amino-N-acetyl-anthranilic acid was obtained in an amount of 450 mg.

(C) Synthesis of 2-acetylamino-4-(N-carbo-benzoxy-L-phenylalanyl-)amino-benzoic acid A solution was prepared by dissolving 493 mg of N-carbobenzoxy-L-phenylalanine and 167 mg of N-methylmorpholine in 5 ml of dry tetrahydrofuran and chilling to a temperature of −15° C. The solution was mixed with 225 mg of isobutyl chloroformate and the resultant mixture was stirred at a temperature of −15° C. to −10° C. for 2 minutes. Then, a solution of 320 mg of 4-amino-N-acetyl anthranilic acid and 167 mg of N-methylmorpholine in 10 ml of dry tetrahydrofuran and 4 ml of dry dimethyl sulfoxide was added dropwise to the mixture, the resultant reaction mixture was stirred at a temperature of −15° C. to −10° C. for one hour, was gradually heated to room temperature, and was further stirred at room temperature for 18 hours. The resultant deposit formed in the reaction mixture was removed by filtration and the remaining filtrate was concentrated under a reduced pressure to provide a yellow oily substance. This oily substance was dissolved in ethyl acetate and the resultant solution was washed with an 1N-hydrochloric acid and then with a saturated brine. The resultant ethyl acetate fraction was dried with anhydrous sodium sulfate, and was concentrated under a reduced pressure to provide 900 mg of a light yellow oily substance. The crude oily substance was purified by a silica gel column chromatography.

2-acetylamino-4-(N-carbobenzoxy-L-phenyl-alanyl-)amino-benzoic acid was obtained in an amount of 595 mg.

(D) Synthesis of 7-(N-carbobenzoxy-L-phenyl-alanyl)amino-2-methyl-4H-3,1-benzoxazin-4-one A solution prepared by dissolving 189 mmg of 2-acetylamino-4-(N-carbobenzoxy-L-phenylalanyl-)aminobenzoic acid in 10 ml of dry tetrahydrofuran was chilled to a temperature of 0° C. The solution was mixed with 167 mg of N,N'-dicyclohexylcarbodiimide and the resultant mixture was gradually heated to room temperature and stirred for 18 hours. The resultant deposit consisting of N,N,-dicyclohexyl-urea was removed by filtration and the remaining filtrate was concentrated under a reduced pressure to provide 261 mg of a light yellow oily substance. This crude oily substance was purified by a silica gel column chromatography and then recrystallized from an ethyl acetate-hexane mixed solvent.

7-(N-carbobenzoxy-L-phenylalanyl)amino-2-methyl-4H-3,1-benzoxazin4-one was obtained in an amount of 91 mg.

1H - NMR (CDCl$_3$, δ ppm)

2.42 (3H, s), 3.1–3.25 (2H, m), 5.04 (2H, s) 5.2–5.6 (2H, m), 7.20 (5H, s), 7.29 (5H, s) 7.1–7.55 (3H, m), 7.9–8.1 (1H, m)

Other 7-(N-A-Y)amino-2-methyl-4H-3,-benzoxazin-4- one compounds indicated in Table 8 can be prepared by the same procedures as mentioned above except that, in the above-mentioned step (C), the amino acid components corresponding to the (N-A-Y) radicals indicated in Table 8 are used in place of the N-carbobenzoxy-L-phenylalanine.

TABLE 8

7-(N-A-Y)amino-2-methyl-4H-3,1-benzoxazin-4-one Compound 7-(N-A-Y)radical 7-(N-carbobenzoxy-L-phenyl-alanyl)
7-(N-carbobenzoxy-L-alanyl)
7-(N-carbobenzoxyglycyl)
7-(N-carbobenzoxy-L-isoleucyl)
7-(N-carbobenzoxy-L-leucyl)
7-(N-carbobenzoxy-L-prolyl)
7-(N-carbobenzoxy-L-valyl)
7-(N-carbobenzoxy-L-norvalyl)
7-(N-carbobenzoxy-L-norleucyl)
7-(N-carbobenzoxy-L-phenyl-glycyl)
7-(N-α,Nε-dicarbobenzoxy-L-glycyl)
7-(N-carbobenzoxy-L-aspartyl)

TABLE 8-continued

| 7-(N-A-Y)amino-2-methyl-4H-3,1-benzoxazin-4-one Compound |
|---|
| 7-(N-A-Y)radical |
| 7-(N-carbobenzoxy-L-glutamyl) |

7-(N-carbobenzoxy-L-aspartyl) 7-(N-carbobenzoxy-L-glutamyl)

EXAMPLE 19

Protease inhibitory activity of 4H-3,1-benzoxazin-4-one compound of the present invention Inhibitory activities of 7-(N-carbobenzoxy-L-phenylalanyl)amino-2-isopropylamino-5-methyl-4H-3,1- benzoxazin-4-one for human purulent sputum elastase, for α-chymotrypsin, for cathepsin G, for trypsin, for thrombin and for plasmin were determined by the following methods and the results are shown in Table 9.

(A) Determination of human purulent soutum elastase-inhibitory activity

Testing buffer

The testing buffer (pH7.5) consisted of 0.1M N-2-hyiroxyethylpiperazine-N'-2-ethanesulfonic acid, 1M sodium chloride and 0.1% w/v polyethylene glycol 6000.

Enzyme

Human purulent sputum elastase was obtained from Elastin Products Co., and adjusted to $1.5 \times 10^{-8}$M in the testing buffer.

Substrate

Methoxysuccinyl-L-alanyl-L-prolyl-L-valyl-p-nitroanilide was obtained from Bachem Co., and made to 10 mM in dimethyl sulfoxide.

Procedure To 2.4ml of testing buffer in a cell set at 37° in a spectrophotometer (Hitachi U-3200) with a temperature controlled cell holder were added 25 μl of substrate solution and 25 μl of acetonitrile with or without inhibitory compounds, and the resultant mixture was stirred. Reactions were initiated by addition of 50 μl of the enzyme solution and hydrolysis of the substrate was monitored by measuring a change of light absorbance at 410 nm. The concentration (IC$_{50}$) at which 50% of the activity of human purulent sputum elastase was inhibited was determined for each inhibitory compound from a steady state velocity of the substrate hydrolysis.

(B) Determination of α-chumotrypsin-inhibitory activity.

The same procedures as those described in the above item (A) for the human purulent sputum elastase were carried out, with the following exception.

The enzyme-testing tuffer solution contained $2 \times 10^{-8}$ M bovine pancreas α-chymotrypsin (available from Sigma Co.). The synthetic substrate was succinyl-L-alanyl-L-alanyl-L-prolyl-L-henylalanyl-p-nitroanilide (available from Bachem Co.).

An IC$_{50}$ for the α-chymotrypsin was determined in the same manner as mentioned above. (C) Determination of human cathepsin G-inhibitory activity The same procedures as those described in the above item (A) were carried out with the following exception.

The enzyme-testing buffer solution contained 2 μg/ml human cathepsin G which was available from Protogen Co. The substrate was succinyl-L-alanyl-L-alanyl-L-prolyl-L-phenylalanyl-p-nitroanilide (available from Bachem Co.).

An IC$_{50}$ for the human cathepsin G was determined in the same manner as mentioned above.

(D) Determination of tryosin-inhibitory activity

The same procedures as those described in item (A) were carried out except that the enzyme-testing buffer solution contained 8 μg/ml bovine pancreas trypsin which was available from Sigma Co., and the substrate consisted of benzyl-arginyl-p-nitroanilide (available from Bachem Co.).

An IC$_{50}$ for the trypsin was determined in the same manner as mentioned above.

(E) Determination of thrombin-inhibitory activity

The same procedures as those described in item (A) were carried out except that the enzyme-testing buffer solution contained 0.04 μkat/ml human thrombin (available from Daiichi Kagaku Yakuhin K.K.) and the substrate consisted of D-phenylalanyl-pipecolyl-arginyl-p-nitroanilide (available from Daiichi Kagaku Yakuhin K.K.).

An ICfor the human thrombin was determined in the same manner as mentioned above.

(F) Determination of plasmin-inhibitory activity

The same procedures as those described in item (A) were carried out except that the enzyme testing buffer solution contained 0.6 CasU/ml human plasmin (available from Daiichi Kagaku Yakuhin K.K.) and the substrate consisted of D-valyl-L-leucyl-L-lysyl-p-nitro-anilide (available from Daiichi Kagaku Yakuhin K.K.).

An IC$_{50}$ for the human plasmin was determined in the same manner as mentioned above.

The results are shown in Table #9.

TABLE 9

| Protease inhibitory activity of 7-(N-carbobenzoxy-L-phenylalanyl)amino-2-isopropylamino-5-methyl-4H-3,1-benzoxazin-4-one | | |
|---|---|---|
| Enzyme | IC(M) 50 | (*)1 Selectivity |
| Human purulent sputum elastase | $1.3 \times 10^{-9}$ | 1 |
| Bovine pancreas α-chymotrypsin | $2.5 \times 10^{-8}$ | 19 |
| Human cathepsin G | $1.1 \times 10^{-7}$ | 85 |
| Bovine pancreds trypsin | $3.0 \times 10^{-6}$ | 2,300 |
| Human thrombin | $>1.0 \times 10^{-4}$ | >100,000 |
| Human Plasmin | $7.5 \times 10^{-5}$ | 58,000 |

Note:(*)1 ... "Selectivity" refers to a ratio of an IC$_{50}$ value for each protease to an IC$_{50}$ value for the human purulent sputum elastase.

EXAMPLES 20 to 37 AND COMPARATIVE EXAMPLE 1 TO 4

In each of Examples 20 to 37 and Comparative Examples 1 to 4, the same experimental procedures as those described in Example 19, items (A) and (B) were used for determination of enzyme inhibitory activity, except that the compound indicated in Table 10 was tested as an inhibitory compound. The results are shown in Table 10.

In Table 10, the item "Selectivity" refers to a ratio of an IC$_{50}$ value for bovine α-chymotrypsin to an IC$_{50}$ value for human purulent sputum elastase. The larger the value of the ratio, the higher the selectivity of the inhibitory activity for elastase.

TABLE 10

Inhibitory compound

[structure diagram showing Y—A—N(H)— attached to benzene ring with R substituent, and C(=O)—O—C(=N—)—X group]

| Example No. | NH—A—Y | R | X | Human purulent sputum elastase IC50 (M) | Bovine α-chymotrypsin IC50 (M) | Selectivity |
|---|---|---|---|---|---|---|
| Example | | | | | | |
| 20 | Z Pro NH (*)$_1$ (*)$_2$ | H | CF$_3$ | $2.2 \times 10^{-6}$ | $1.7 \times 10^{-5}$ | 7.7 |
| 21 | Z Pro NH | H | OiPr (*)$_3$ | $4.4 \times 10^{-8}$ | $1.7 \times 10^{-7}$ | 3.9 |
| 22 | Z Ala NH (*)$_4$ | H | OiPr | $7.7 \times 10^{-8}$ | $3.7 \times 10^{-7}$ | 4.8 |
| 23 | Z Val NH (*)$_5$ | H | OiPr | $2.4 \times 10^{-8}$ | $1.6 \times 10^{-7}$ | 6.6 |
| 24 | Z Phe NH (*)$_6$ | H | OiPr | $1.1 \times 10^{-8}$ | $3.4 \times 10^{-7}$ | 31 |
| 25 | Z Lys (Z) NH (*)$_7$ | H | OiPr | $1.4 \times 10^{-8}$ | $5.8 \times 10^{-7}$ | 41 |
| 26 | Z Glu (OBzl) NH (*)$_8$ | H | OiPr | $2.6 \times 10^{-8}$ | $>5.0 \times 10^{-7}$ | >20 |
| 27 | Z-D-Phe NH (*)$_9$ | H | OiPr | $4.1 \times 10^{-8}$ | $4.9 \times 10^{-7}$ | 12 |
| 28 | Boc Pro NH (*)$_{10}$ | H | OiPr | $3.5 \times 10^{-8}$ | $1.3 \times 10^{-7}$ | 3.7 |
| 29 | Boc Phe NH | H | OiPr | $4.6 \times 10^{-8}$ | $9.4 \times 10^{-8}$ | 2.0 |
| 30 | Ac Pro NH (*)$_{11}$ | H | OiPr | $1.3 \times 10^{-7}$ | $4.9 \times 10^{-7}$ | 3.8 |
| 31 | Z Ala Pro NH | H | OiPr | $3.2 \times 10^{-8}$ | $1.8 \times 10^{-7}$ | 5.6 |
| 32 | Z Pro Val NH | H | OiPr | $2.0 \times 10^{-8}$ | $1.2 \times 10^{-7}$ | 5.8 |
| 33 | Z Phe Val NH | H | OiPr | $2.1 \times 10^{-8}$ | $1.8 \times 10^{-7}$ | 5.6 |
| 34 | Z Phe NH | CH$_3$ | OiPr | $5.5 \times 10^{-10}$ | $1.0 \times 10^{-8}$ | 18 |
| 35 | Z Phe NH | H | NHiPr (*)$_{12}$ | $4.3 \times 10^{-8}$ | $7.0 \times 10^{-8}$ | 17 |
| 36 | Z Phe NH | CH$_3$ | NHiPr | $1.3 \times 10^{-9}$ | $2.5 \times 10^{-8}$ | 19 |
| 37 | Z Pre NH | H | CH$_3$ | $5.1 \times 10^{-6}$ | $1.6 \times 10^{-4}$ | 31 |
| Comparative Example | | | | | | |
| 1 | H | H | CF$_3$ | $6.2 \times 10^{-6}$ | $6.8 \times 10^{-7}$ | 0.10 |
| 2 | H | H | OiPr | $4.9 \times 10^{-8}$ | $2.2 \times 10^{-8}$ | 0.44 |
| 3 | AcNH | H | OiPr | $5.8 \times 10^{-8}$ | $3.2 \times 10^{-8}$ | 0.55 |
| 4 | H | CH$_3$ | OiPr | $4.1 \times 10^{-8}$ | $1.2 \times 10^{-7}$ | 2.9 |

Note:
(*)$_1$ Z — Carbobenzoxy radical,

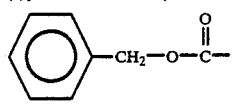

(*)$_2$ Pro — Prolyl radical
(*)$_3$ OiPr — Isopropoxy radical
(*)$_4$ Ala — Alanyl radical
(*)$_5$ Val — Valyl radical
(*)$_6$ Phe — Phenylalanyl radical
(*)$_7$ Lys(Z) — N-ε-carbobenzoxylysyl radical
(*)$_8$ Glu(OBzl) — Glutamic acid γ-benzyl ester
(*)$_9$ D-Phe — D-phenylalanyl radical
(*)$_{10}$ Boc — N-tert-butoxycarbonyl radical
(*)$_{11}$ Ac — Acetyl radical
(*)$_{12}$ NHiPr — Isopropylamino radical

EXAMPLE 38

Stability of 4H-3,1-benzoxazin-4-one compound of the present invention in human serum A solution of 10 mmoles of 7-(N-carbobenzoxy-L-phenylalanyl)amino-2-isopropylamino-5-methyl-4H-3,1-benzoxazin-4-one in 50 μl acetonitrile was mixed with 0.45 ml of human serum, and the resultant mixture was allowed to stand at a temperature of 37° C. The mixture was subjected to treatment with a Sep-pac C$_{18}$ cartridge (trademark, made by Waters Cc.) for removal of protein, and a portion of the resultant acetonitrile-eluted fraction was subjected to a high speed liquid chromatographic analysis. In analysis, a half life for the stability of the compound is represented by a standing time at 37° C., in which the peak area of the compound decreased to 50% of the original peak area of the compound before standing at 37° C.

As a result, the half life for the stability of the tested compound in human serum was 150 minutes.

INDUSTRIAL APPLICABILITY

The specific 4H-3,1-benzoxazin-4-one compounds of the present invention are useful as a protease inhibitor, particularly as an elastase inhibitor, and are effective for blocking or abating inflammation, degeneration and destruction of tissues caused by the action of proteases, particularly elastase, on animal, particularly human, elastin and other proteins.

We claim:

1. 4H-3,1-benzoxazin-4-one compounds of the formula (I):

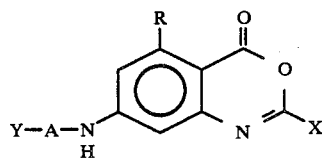

wherein

R represents a member selected from the group consisting of a hydrogen atom and methyl and ethyl radicals;

A represents an amino acid residue selected from the group consisting of alanine, glycine, isoleucine, leucine, phenylalanine, proline, valine, norvaline, norleucine, phenylglycine, lysine having an ε-amino radical protected by a carbobenzoxy radical, aspartic acid having a β-carboxyl radical protected in the form of a benzyl ester thereof, glutamic acid having a γ-carboxylic protected in the form of a benzyl ester thereof and peptides having 2 to 3 of said amino acid residues, wherein said amino acid residues optionally have a side chain protected by protective radicals;

X represents a member selected from the group consisting of $OR^1$ radicals and $NHR^1$ radicals in which $R^1$ represents an alkyl radical; and Y represents a protective radical for an amino radical selected from the group consisting of carbobenzyoxy, tert-butoxycarbonyl, and acetyl radicals, and salts thereof.

2. The compound as claimed in claim 1, wherein the $OR^1$ radical represented by X in the formula (I) is selected from the group consisting of methoxy, ethoxy, propoxy, isopropoxy, butoxy and isobutoxy radicals.

3. The compound as claimed in claim 1, wherein the $NHR^1$ radical represented by X in the formula (I) is selected from the group consisting of monomethylamino, monoethylamino, monopropylamino, monoisopropylamino, monobutylamino, and monoisobutylamino radicals.

4. Pharmaceutical compositions for the inhibition of serine proteases comprising a mixture of a pharmaceutically effective amount of the 4H-3,1-benzoxazin-4-one compound of the formula (I) as claimed in claim 1 or a pharmaceutically acceptable non-toxic salt thereof and a pharmaceutically acceptable carrier thereof.

5. The composition as claimed in claim 4, wherein the serine protease is a human leukocyte elastase.

* * * * *